(12) United States Patent
Halstead et al.

(10) Patent No.: US 12,268,824 B2
(45) Date of Patent: *Apr. 8, 2025

(54) SHAPED CATHETER TIP FOR TRACKING OVER A GUIDEWIRE THROUGH TURNS IN THE VASCULATURE

(71) Applicant: Embolx, Inc., Sunnyvale, CA (US)

(72) Inventors: Greg Halstead, Sunnyvale, CA (US); Arturo Viscorra, San Jose, CA (US)

(73) Assignee: Embolx, Inc., Sunnyvale, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/047,922

(22) Filed: Jul. 27, 2018

(65) Prior Publication Data

US 2020/0030577 A1    Jan. 30, 2020

(51) Int. Cl.
*A61M 25/01* (2006.01)
*A61M 25/00* (2006.01)
*A61M 25/10* (2013.01)

(52) U.S. Cl.
CPC ...... *A61M 25/0147* (2013.01); *A61M 25/005* (2013.01); *A61M 25/1002* (2013.01); *A61M 25/0113* (2013.01); *A61M 25/0141* (2013.01)

(58) Field of Classification Search
CPC .......... A61M 25/0041; A61M 25/0045; A61M 25/005; A61M 25/0054; A61M 25/0067;
(Continued)

(56) References Cited

U.S. PATENT DOCUMENTS 4,198,981 A   4/1980 Sinnreich
4,545,390 A * 10/1985 Leary .............. A61M 25/09033
                                              600/462
(Continued)

FOREIGN PATENT DOCUMENTS

CN       101400400 A    4/2009
CN       102159277 A    8/2011
(Continued)

OTHER PUBLICATIONS

Angiodynamics; Soft-vu angiographic catheters; 2 pages; retrieved from the internet (http://www.angiodynamics.com/products/soft-vu) on Aug. 17, 2018.
(Continued)

*Primary Examiner* — Kami A Bosworth
(74) *Attorney, Agent, or Firm* — Shay Glenn LLP (57) ABSTRACT

A vascular catheter system is provided with a flexible main body and a flexible shaped tip. The tip is located at the distal end of the main body and has at least a portion configured to deviate from a longitudinal axis when in a relaxed state and towards alignment with the longitudinal axis when a guidewire is extended through a lumen of the shaped tip. The shaped tip is no longer than 1 cm and includes at least three sections. The second section is located distally from the first section, and the third section is located distally from the second section. The second section includes a first material having a first durometer and a second material having a second durometer lower than the first durometer. The first section includes the first material without the second material, and the third section includes the second material without the first material.

13 Claims, 5 Drawing Sheets

(58) Field of Classification Search
CPC ............ A61M 25/0074; A61M 25/008; A61M 25/0108; A61M 25/0113; A61M 25/0141; A61M 25/0147; A61M 25/09; A61M 25/10; A61M 25/1002; A61M 2025/0042; A61M 2025/0081; A61M 2025/0161; A61M 2025/09175

See application file for complete search history.

(56) References Cited

U.S. PATENT DOCUMENTS

| | | | |
|---|---|---|---|
| 4,581,017 A | 4/1986 | Sahota | |
| 4,737,153 A | 4/1988 | Shimamura et al. | |
| 4,748,982 A | 6/1988 | Horzewski et al. | |
| 4,892,519 A | 1/1990 | Songer et al. | |
| 4,896,669 A | 1/1990 | Bhate et al. | |
| 4,898,591 A * | 2/1990 | Jang | A61L 29/049 604/527 |
| 4,909,252 A | 3/1990 | Goldberger | |
| 4,944,745 A | 7/1990 | Sogard et al. | |
| 4,976,690 A | 12/1990 | Solar et al. | |
| 4,990,143 A | 2/1991 | Sheridan | |
| 5,000,734 A | 3/1991 | Boussignac et al. | |
| 5,040,548 A | 8/1991 | Yock | |
| 5,045,072 A * | 9/1991 | Castillo | A61M 25/0054 604/529 |
| 5,047,045 A | 9/1991 | Arney et al. | |
| 5,078,685 A | 1/1992 | Colliver | |
| 5,090,958 A | 2/1992 | Sahota | |
| 5,100,386 A | 3/1992 | Inoue | |
| 5,137,513 A | 8/1992 | Mcinnes et al. | |
| 5,156,594 A | 10/1992 | Keith et al. | |
| 5,217,434 A | 6/1993 | Arney | |
| 5,234,416 A * | 8/1993 | Macaulay | A61M 25/008 600/435 |
| 5,254,107 A * | 10/1993 | Soltesz | A61M 25/005 604/525 |
| 5,279,562 A | 1/1994 | Sirhan et al. | |
| 5,334,154 A | 8/1994 | Samson et al. | |
| 5,342,386 A | 8/1994 | Trotta | |
| 5,356,388 A | 10/1994 | Sepetka et al. | |
| 5,370,655 A | 12/1994 | Burns | |
| 5,423,754 A | 6/1995 | Cornelius et al. | |
| 5,423,829 A | 6/1995 | Pham et al. | |
| 5,429,605 A | 7/1995 | Richling: Bernd | |
| 5,454,795 A | 10/1995 | Samson | |
| 5,470,314 A | 11/1995 | Walinsky | |
| 5,484,409 A | 1/1996 | Atkinson et al. | |
| 5,498,251 A | 3/1996 | Dalton | |
| 5,501,667 A | 3/1996 | Verduin | |
| 5,509,910 A | 4/1996 | Lunn | |
| 5,538,510 A | 7/1996 | Fontirroche et al. | |
| 5,556,383 A | 9/1996 | Wang et al. | |
| 5,582,619 A | 12/1996 | Ken | |
| 5,584,821 A | 12/1996 | Hobbs et al. | |
| 5,588,442 A | 12/1996 | Scovil et al. | |
| 5,599,326 A | 2/1997 | Carter | |
| 5,624,449 A | 4/1997 | Pham et al. | |
| 5,637,086 A | 6/1997 | Ferguson et al. | |
| 5,643,254 A | 7/1997 | Scheldrup et al. | |
| 5,647,198 A | 7/1997 | Mihailovic | |
| 5,649,949 A | 7/1997 | Wallace et al. | |
| 5,658,263 A * | 8/1997 | Dang | A61M 25/0041 604/264 |
| 5,669,905 A | 9/1997 | Scheldrup et al. | |
| 5,674,198 A | 10/1997 | Leone | |
| 5,690,666 A | 11/1997 | Berenstein et al. | |
| 5,690,667 A | 11/1997 | Gia | |
| 5,718,711 A | 2/1998 | Berenstein et al. | |
| 5,722,424 A | 3/1998 | Engelson | |
| 5,749,837 A | 5/1998 | Palermo et al. | |
| 5,766,192 A | 6/1998 | Zacca | |
| 5,769,830 A | 6/1998 | Parker | |
| 5,775,327 A * | 7/1998 | Randolph | A61M 25/0054 600/374 |
| 5,792,300 A | 8/1998 | Inderbitzen et al. | |
| 5,797,874 A | 8/1998 | Spears | |
| 5,800,454 A | 9/1998 | Jacobsen et al. | |
| 5,807,355 A | 9/1998 | Ramzipoor et al. | |
| 5,820,592 A * | 10/1998 | Hammerslag | A61M 25/0152 604/95.01 |
| 5,830,182 A | 11/1998 | Wang et al. | |
| 5,833,705 A | 11/1998 | Ken et al. | |
| 5,843,032 A | 12/1998 | Kastenhofer | |
| 5,843,050 A | 12/1998 | Jones et al. | |
| 5,851,203 A | 12/1998 | Van Muiden | |
| 5,853,418 A | 12/1998 | Ken et al. | |
| 5,868,704 A | 2/1999 | Campbell et al. | |
| 5,879,324 A | 3/1999 | von Hoffmann | |
| 5,891,128 A | 4/1999 | Gia et al. | |
| 5,911,717 A | 6/1999 | Jacobsen et al. | |
| 5,938,653 A * | 8/1999 | Pepin | B29C 48/34 604/523 |
| 5,951,539 A | 9/1999 | Nita et al. | |
| 5,951,929 A | 9/1999 | Wilson | |
| 5,984,878 A | 11/1999 | Engelson | |
| 5,984,929 A | 11/1999 | Bashiri et al. | |
| 6,013,084 A | 1/2000 | Ken et al. | |
| 6,014,919 A | 1/2000 | Jacobsen et al. | |
| 6,019,757 A | 2/2000 | Scheldrup | |
| 6,022,340 A | 2/2000 | Sepetka et al. | |
| 6,036,382 A | 3/2000 | Lange et al. | |
| 6,036,670 A | 3/2000 | Wijeratne et al. | |
| 6,066,157 A | 5/2000 | Barbere | |
| 6,066,667 A | 5/2000 | Ashbrook | |
| 6,071,286 A | 6/2000 | Mawad | |
| 6,090,099 A | 7/2000 | Samson et al. | |
| 6,103,037 A * | 8/2000 | Wilson | B29C 66/1142 264/254 |
| 6,123,714 A | 9/2000 | Gia et al. | |
| 6,156,061 A | 12/2000 | Wallace et al. | |
| 6,165,163 A | 12/2000 | Chien et al. | |
| 6,187,027 B1 | 2/2001 | Mariant et al. | |
| 6,190,358 B1 | 2/2001 | Fitzmaurice et al. | |
| 6,190,393 B1 | 2/2001 | Bevier et al. | |
| 6,203,547 B1 | 3/2001 | Nguyen et al. | |
| 6,258,080 B1 | 7/2001 | Samson | |
| 6,270,495 B1 | 8/2001 | Palermo | |
| 6,280,457 B1 | 8/2001 | Wallace et al. | |
| 6,287,301 B1 | 9/2001 | Thompson et al. | |
| 6,319,228 B1 | 11/2001 | Kastenhofer | |
| 6,344,041 B1 | 2/2002 | Kupiecki et al. | |
| 6,397,850 B1 | 6/2002 | Scheldrup et al. | |
| 6,423,085 B1 | 7/2002 | Murayama et al. | |
| 6,428,489 B1 | 8/2002 | Jacobsen et al. | |
| 6,440,088 B1 | 8/2002 | Jacobsen et al. | |
| 6,468,266 B1 | 10/2002 | Bashiri et al. | |
| 6,471,673 B1 | 10/2002 | Kastenhofer | |
| 6,508,804 B2 | 1/2003 | Sarge et al. | |
| 6,553,880 B2 | 4/2003 | Jacobsen et al. | |
| 6,575,959 B1 | 6/2003 | Sarge et al. | |
| 6,579,246 B2 | 6/2003 | Jacobsen et al. | |
| 6,635,069 B1 | 10/2003 | Teoh et al. | |
| 6,638,245 B2 | 10/2003 | Miller et al. | |
| 6,648,874 B2 * | 11/2003 | Parisi | A61L 29/085 604/525 |
| 6,652,508 B2 | 11/2003 | Griffin et al. | |
| 6,656,550 B1 | 12/2003 | Zamore | |
| 6,702,782 B2 | 3/2004 | Miller et al. | |
| 6,702,802 B1 | 3/2004 | Hancock et al. | |
| 6,706,025 B2 | 3/2004 | Engelson et al. | |
| 6,766,720 B1 | 7/2004 | Jacobsen et al. | |
| 6,780,181 B2 | 8/2004 | Kroll et al. | |
| 6,835,189 B2 | 12/2004 | Musbach et al. | |
| 6,849,062 B2 | 2/2005 | Kantor | |
| 6,860,893 B2 | 3/2005 | Wallace et al. | |
| 6,860,899 B1 | 3/2005 | Rivelli | |
| 6,878,151 B2 | 4/2005 | Carrison et al. | |
| 6,921,410 B2 | 7/2005 | Porter | |
| 6,936,055 B1 | 8/2005 | Ken et al. | |
| 6,997,937 B2 | 2/2006 | Jacobsen et al. | |
| 7,004,962 B2 | 2/2006 | Stinson | |
| 7,037,330 B1 | 5/2006 | Rivelli et al. | |
| 7,060,083 B2 | 6/2006 | Gerberding | |

(56) References Cited

U.S. PATENT DOCUMENTS

| | | |
|---|---|---|
| 7,070,607 B2 | 7/2006 | Murayama et al. |
| 7,144,407 B1 | 12/2006 | Lasersohn |
| 7,153,323 B1 | 12/2006 | Teoh et al. |
| 7,166,122 B2 | 1/2007 | Aganon et al. |
| 7,294,137 B2 | 11/2007 | Rivelli et al. |
| 7,332,689 B2 | 2/2008 | Mertens et al. |
| 7,412,285 B2 | 8/2008 | Schroeppel et al. |
| 7,468,070 B2 | 12/2008 | Henry et al. |
| 7,481,800 B2 | 1/2009 | Jacques |
| 7,621,904 B2 | 11/2009 | McFerran et al. |
| 7,645,259 B2 | 1/2010 | Goldman |
| 7,654,979 B2 | 2/2010 | Simpson |
| 7,742,811 B2 | 6/2010 | Schroeppel et al. |
| 7,780,626 B2 | 8/2010 | Wu et al. |
| 7,942,847 B2 | 5/2011 | Stupecky et al. |
| 7,998,165 B2 | 8/2011 | Huffmaster |
| 8,066,667 B2 | 11/2011 | Hayman et al. |
| 8,092,508 B2 | 1/2012 | Leynov et al. |
| 8,202,292 B2 | 6/2012 | Kellett |
| 8,206,373 B2 | 6/2012 | Zhou |
| 8,348,890 B2 | 1/2013 | Gerrans et al. |
| 8,961,550 B2 | 2/2015 | Lenker et al. |
| 9,005,163 B2 | 4/2015 | Bonnette et al. |
| 9,174,020 B2 | 11/2015 | Allen et al. |
| 9,205,226 B2 | 12/2015 | Allen et al. |
| 9,427,550 B2 | 8/2016 | Dakin et al. |
| 9,550,046 B1 | 1/2017 | Allen |
| 9,555,165 B2 | 1/2017 | Phan |
| 9,844,383 B2 | 12/2017 | Allen |
| 10,086,174 B2 | 10/2018 | Crall et al. |
| 2001/0041862 A1 | 11/2001 | Glickman |
| 2002/0004666 A1 | 1/2002 | Schwager et al. |
| 2002/0032457 A1 | 3/2002 | Sirhan et al. |
| 2002/0193820 A1 | 12/2002 | Wakuda et al. |
| 2003/0050600 A1 | 3/2003 | Ressemann et al. |
| 2003/0114878 A1 | 6/2003 | Diederich et al. |
| 2003/0144657 A1* | 7/2003 | Bowe .............. A61M 25/0026 606/41 |
| 2003/0180488 A1 | 9/2003 | Lim et al. |
| 2003/0191435 A1 | 10/2003 | Shkolnik |
| 2003/0199914 A1 | 10/2003 | Diaz |
| 2003/0220628 A1 | 11/2003 | Kilsch et al. |
| 2004/0015151 A1 | 1/2004 | Chambers |
| 2004/0073158 A1* | 4/2004 | Shah .............. A61M 25/0662 604/19 |
| 2004/0167415 A1 | 8/2004 | Gelfand et al. |
| 2005/0131453 A1 | 6/2005 | Parodi |
| 2005/0267407 A1 | 12/2005 | Goldman |
| 2006/0106413 A1 | 5/2006 | Bence et al. |
| 2006/0149186 A1 | 7/2006 | Wantink et al. |
| 2006/0276886 A1 | 12/2006 | George et al. |
| 2007/0088380 A1 | 4/2007 | Hirszowicz et al. |
| 2007/0137651 A1 | 6/2007 | Glassenberg et al. |
| 2007/0149927 A1 | 6/2007 | Itou et al. |
| 2008/0033372 A1 | 2/2008 | Briscoe et al. |
| 2008/0045908 A1 | 2/2008 | Gould et al. |
| 2008/0208118 A1 | 8/2008 | Goldman |
| 2008/0262470 A1 | 10/2008 | Lee et al. |
| 2009/0131831 A1 | 5/2009 | Wright et al. |
| 2009/0156999 A1 | 6/2009 | Adams et al. |
| 2009/0177183 A1 | 7/2009 | Pinkernell et al. |
| 2010/0030200 A1 | 2/2010 | Strauss et al. |
| 2010/0113939 A1 | 5/2010 | Mashimo et al. |
| 2010/0222637 A1 | 9/2010 | Kassab |
| 2010/0249491 A1 | 9/2010 | Farnan et al. |
| 2012/0203173 A1 | 8/2012 | Davies et al. |
| 2012/0253447 A1 | 10/2012 | Hayasaka et al. |
| 2013/0131610 A1 | 5/2013 | Dewaele et al. |
| 2014/0163421 A1 | 6/2014 | Van Hoven |
| 2014/0371709 A1 | 12/2014 | Allen et al. |
| 2014/0371718 A1 | 12/2014 | Alvarez et al. |
| 2015/0112255 A1 | 4/2015 | Jensen et al. |
| 2015/0351729 A1 | 12/2015 | Chin et al. |
| 2016/0008585 A1 | 1/2016 | Tano |
| 2016/0096002 A1 | 4/2016 | Di Caprio et al. |
| 2016/0101261 A1 | 4/2016 | Kugler et al. |
| 2016/0158439 A1 | 6/2016 | Allen |
| 2016/0199067 A1 | 7/2016 | Smith et al. |
| 2016/0213893 A1 | 7/2016 | Franklin |
| 2017/0049495 A1 | 2/2017 | Yu et al. |
| 2017/0095646 A1 | 4/2017 | Norman et al. |
| 2017/0252542 A1 | 9/2017 | Iwano et al. |
| 2017/0303890 A1 | 10/2017 | Yamashita |
| 2018/0015248 A1 | 1/2018 | Logan et al. |
| 2018/0056036 A1 | 3/2018 | Wada et al. |
| 2018/0125502 A1 | 5/2018 | Allen |
| 2019/0329007 A1 | 10/2019 | Allen et al. |
| 2023/0226328 A1 | 7/2023 | Roewer et al. |

FOREIGN PATENT DOCUMENTS

| | | |
|---|---|---|
| CN | 102802698 A | 11/2012 |
| CN | 102805893 A | 12/2012 |
| CN | 103987421 A | 8/2014 |
| CN | 105246537 A | 1/2016 |
| CN | 105854151 A | 8/2016 |
| CN | 106422033 A | 2/2017 |
| DE | 102009025347 A1 | 12/2010 |
| DE | 202011003097 U1 | 7/2011 |
| EP | 0520692 S1 | 12/1992 |
| EP | 1131126 B1 | 8/2004 |
| EP | 2389968 A2 | 11/2011 |
| EP | 3132823 A1 | 2/2017 |
| GB | 2512696 A | 10/2014 |
| JP | H03-207376 A | 9/1991 |
| JP | H05-15604 A | 1/1993 |
| JP | H06-277296 A | 10/1994 |
| JP | H07-213617 A | 8/1995 |
| JP | H10244006 A | 9/1998 |
| JP | 2003500121 A | 1/2003 |
| JP | 2005511108 A | 4/2005 |
| JP | 2006511271 A | 4/2006 |
| JP | 2007319468 A | 12/2007 |
| JP | 2008522716 A | 7/2008 |
| JP | 2008544801 A | 12/2008 |
| JP | 2011087971 A | 5/2011 |
| JP | 2011152181 A | 8/2011 |
| JP | 201290779 A | 5/2012 |
| JP | 2015523884 A | 8/2015 |
| JP | 2016591778 A | 6/2016 |
| KR | 20100006710 U | 7/2010 |
| WO | WO89/08471 A1 | 9/1989 |
| WO | WO99/48548 A1 | 9/1999 |
| WO | WO2004/107965 A2 | 12/2004 |
| WO | WO2007/121005 A1 | 10/2007 |
| WO | WO2012/009486 A2 | 1/2012 |
| WO | WO2012/099979 A1 | 7/2012 |
| WO | WO2014/008489 A1 | 1/2014 |
| WO | WO2019/236951 A1 | 12/2019 |
| WO | WO2020/023889 A1 | 1/2020 |

OTHER PUBLICATIONS

BMI ESPICOM Pharmaceutical and Medical Device News; Business Monitor Online: Vascular solutions expands complex intervention offerings with turnpike LP catheter; newsletter; 2pages; retrieved from the internet (https://dialog.proquest.com/professional/docview/1753127273?accountid=157282) on Apr. 18, 2018 (Abstract Only).

Cliffton et al.; Technique for visualization and perfusion of bronchial arteries: suggested clinical and diagnostic applications; Cancer; 16; pp. 444-452; Apr. 1963.

Matsuda et al.; Electrospinning fabrication of high-trackable catheter tip with gradually graded or gradient flexibility; J. Biomed. Mater. Res. B Appl. Biomater.; 1(35); pp. 35-41 doi: 10.1002/jbm.b.31061; (Abstract Only); Oct. 2008.

Nordson Medical; Extruded tubing technical information; 7 pages; retrieved from the internet (https://www.nordsonmedical.com/Components-and-Technologies/Medical-Tubing/Extruded-Tubing/Technical-Information/) on Aug. 17, 2018.

Rousselot et al.; Selective concentration of anticancer drugs in the liver: Hepatic-artery infusion and induced hepatic outflow block; JAMA; 191(9); pp. 707-710; Mar. 1965.

(56) References Cited

OTHER PUBLICATIONS

Vante Plasticweld Systems; Bonds and welds; 13 pages; retrieved from the internet (https://cathetertipping.com/home/our-products/bonding/) on Aug. 17, 2018.
Worldwide Videotex; Angiodynamics PCTA balloon catheter gets FDA market clearance; Biotech Equipment Update 5.9: N/A. Worldwide Videotex; Sep. 1, 1997; 2 pages; retrieved from the internet (https://dialog.proquest.com/professional/docview/680080033?accountid=157282) on Apr. 18, 2018 (Abstract Only).
Zeus; FluoroPEELZ peelable heat shrink; 9 pages; retrieved from the internet (https://www.zeusinc.com/products/heat-shrinkable-tubing/fluoropeelz-peelable-heat-shrink) on Aug. 17, 2018.
Allen et al.; U.S. Appl. No. 15/413,262 entitled "Balloon catheter and methods of fabrication and use," filed Jan. 23, 2017.
Halstead et al.; U.S. Appl. No. 16/004,247 entitled "High torque catheter and methods of manufacture," filed Jun. 8, 2018.
Allen; U.S. Appl. No. 16/889,379 entitled "Devices and methods for low pressure tumor embolization," filed Jun. 1, 2020.
Allen U.S. Appl. No. 16/196,398 entitled "Device and methods for transvascular tumor embolization," filed Nov. 20, 2018.
Cook Medical; Flexor technology; 16 pages; retrieved from the internet (https:cookmedical.com/data/resources/PI-BM-KCF-EN-201302_WEB.pdf) on May 5, 2019.
Halstead et al.; U.S. Appl. No. 16/545,519 entitled "Balloon catheters and methods of manufacture and use," filed Aug. 20, 2019.
Halstead et al.; U.S. Appl. No. 17/636,562 entitled "Catheters and methods of manufacture and use," filed Feb. 18, 2022.
Halstead et al.; U.S. Appl. No. 17/938,559 entitled "Balloon catheters and methods of manufacture and use," filed Oct. 6, 2022.

\* cited by examiner

RELAXED

FIG. 7A

10mm EXTENSION

FIG. 7B

30mm EXTENSION

FIG. 7C

80mm EXTENSION

FIG. 7D

SHAPED CATHETER TIP FOR TRACKING OVER A GUIDEWIRE THROUGH TURNS IN THE VASCULATURE

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

Described herein are tip components, devices, systems and methods for effectively steering a catheter through turns in the vasculature.

BACKGROUND

Catheters are commonly used in medicine for delivery of fluids, therapeutics and implants as well as in sampling tissues and bodily fluids. Catheters can be constructed with balloons or other tools to dilate tissue, block fluid flow or isolate segments of the anatomy. A relatively common use for a catheter is the delivery of drugs to a target tissue using blood vessels as a means of access. When a balloon is used, the vascular compartment distal to the balloon is isolated from the vascular compartment proximal to the balloon and perfusion of diagnostic, therapeutic or embolic agents is localized and concentrated. Transvascular catheters, especially in the peripheral blood circulation, need to have a small diameter to allow access into small vessels.

One common use for a microcatheter is the delivery of embolic agents and anticancer drugs to a tumor.

According to the NIH, 30,640 people were diagnosed with primary liver cancer (hepatocellular carcinoma, HCC) and 142,820 people were diagnosed with colorectal cancer in the US in 2013. Seventy five percent of these will metastasize to the liver. Liver resection and transplant are the only curative means; however, only small numbers of patients are eligible. Systemic Chemotherapy for primary and metastatic tumors in the liver is ineffective, having a response rate of about 20% and a survival benefit of 10.7 months vs. 7.9 months over symptomatic care.

Trans-Arterial Embolization therapy is the transvascular access for injection of drug and/or embolic agents directly into, or in the vicinity of, the tumor vasculature using a microcatheter. Embolization therapy causes a shutdown of blood flow and, when drug or radioactivity is present, simultaneous release of high concentrations of drug or radioactivity. The technique is also noted for its very low level of toxicity. Chemoembolization was established as a standard of care for intermediate stage hepatocellular carcinoma in 2006. Numerous studies have demonstrated transarterial embolization to be effective on a number of primary cancers and to have better performance than chemotherapy for both HCC and metastatic colorectal cancers in the liver.

Various prior art references provide guidance on aspects of medical catheter construction. For example, U.S. patent application Ser. No. 10/128,977 describes a coaxial catheter whereby a balloon is bonded to an elongated outer tube to prevent the balloon from telescopingly buckling when the balloon is being pushed across a narrow passage. U.S. Pat. No. 6,066,157 describes a coaxial coronary angioplasty catheter whereby an anchor joint is configured to allow distal movement of the inner tube and to prevent proximal movement. U.S. Pat. No. 5,647,198 describes a catheter with a pair of spaced apart balloons that define an intra-balloon space. A lumen passes through the catheter and exits within the intra-balloon space allowing injection of drugs, emulsions, fluids and fluid/solid mixtures. A perfusion lumen or bypass extends from a location proximal to the proximal balloon and to the distal tip to allow shunting of blood past the inflated balloons. U.S. Pat. No. 5,674,198 describes a two balloon catheter that is designed for treating a solid tumor. The balloons are positioned to isolate the blood flow into the tumor and allow injection of a vaso-occlusive collagen material to block the tumor blood supply. Clifton et al. (1963) Cancer 16:444-452 describes a two balloon catheter for the treatment of lung carcinoma. The four lumen catheter includes a lumen for independent injection in the space between the balloons. Rousselot et al. (1965) JAMA 191:707-710 describes a balloon catheter device for delivering anticancer drugs into the liver. See also U.S. Pat. Nos. 6,780,181; 6,835,189; 7,144,407; 7,412,285; 7,481,800; 7,645,259; 7,742,811; U.S. App. No. 2001/008451; U.S. App. No. 2001/0041862; U.S. App. No. 2003/008726; U.S. App. No. 2003/0114878; U.S. App. No. 2005/0267407; U.S. App. No. 2007/0137651; U.S. App. No. 2008/0208118; U.S. App. No. 2009/0182227 and U.S. App. No. 2010/0114021.

Medical catheters often are advanced through torturous vasculature, requiring a flexible distal section that can easily follow the vessel and a stiff proximal section that can support longitudinal advancement of the catheter as it twists and turns through the blood vessels. It is also desirable, in certain applications, that the catheter can transmit torque throughout its length, from the proximal end to the distal tip. This is particularly true when a shaped catheter tip is used. Shaped catheter tips are common and used to direct a guidewire and/or a catheter around acute angles and into branch vessels. A 90-degree shape is among the favored tip configurations. In use, the catheter tip is rotationally oriented so that the angled tip is pointed toward the desired direction of travel and then the guidewire is further advanced into the vasculature. However, tracking a catheter through tortuous vasculature remains a challenging and time consuming process.

Accordingly, there remains an unmet medical need for an improved catheter having a shaped tip that facilitates navigation through tortuous vasculature.

SUMMARY OF THE DISCLOSURE

In some embodiments of the present disclosure, a vascular catheter system is provided with a flexible main body and a flexible shaped tip. The flexible main body extends along a generally straight longitudinal axis when in a relaxed state and has a proximal end and a distal end. The main body also has a lumen therethrough configured to slidably receive a guidewire. The flexible shaped tip is located at the distal end of the main body. The shaped tip has a lumen therethrough that is in communication with the lumen of the main body and is configured to slidably receive a guidewire. The shaped tip has at least a portion configured to deviate from the longitudinal axis when in a relaxed state and configured to move towards alignment with the longitudinal axis when a guidewire is extended through the lumen of the shaped tip. The shaped tip is no longer than 1 cm and comprises at least three sections including a first, a second and a third section. The second section is located distally from the first section and the third section is located distally from the second section. The second section includes a first material having a first durometer and a second material having a second durometer lower than the first durometer. The second material includes a polymer and tungsten. The first section includes the first material without the second material, and the third section includes the second material without the first material.

In some of the above embodiments, the portion of the shaped tip configured to deviate from the longitudinal axis extends through an angle of at least 30 degrees. The portion of the shaped tip configured to deviate from the longitudinal axis may extend through an angle of between about 60 and about 90 degrees. In some embodiments, the portion of the shaped tip configured to deviate from the longitudinal axis extends through an angle of between about 120 and about 160 degrees.

Some embodiments of the system further include a guidewire configured to be received through the main body and the shaped tip to guide a distal end of the shaped tip through torturous vasculature. A distal region of the guidewire may increase in stiffness when moving from its distal end towards its proximal end. The system may further include an inflatable balloon located near the distal end of the main body.

In some embodiments, the shaped tip includes a single bend. In other embodiments, the shaped tip includes at least two bends. The shaped tip may include a curved portion having an inner bend radius no greater than about 0.10 inches. The shaped tip may include a curved portion having an inner bend radius no greater than about three times an outside diameter of the shaped tip.

In some embodiments of the present disclosure, a method of manufacturing a vascular catheter system is provided. The method may include the steps of providing a flexible main body, and forming and bonding a flexible shaped tip to the distal end of the main body. The flexible main body may extend along a generally straight longitudinal axis when in a relaxed state. The main body has a proximal end and a distal end and may have a lumen therethrough configured to slidably receive a guidewire. The shaped tip may be provided with a lumen therethrough in communication with the lumen of the main body and configured to slidably receive a guidewire. In some embodiments, the shaped tip has at least a portion configured to deviate from the longitudinal axis when in a relaxed state and configured to move towards alignment with the longitudinal axis when a guidewire is extended through the lumen of the shaped tip. In some embodiments, the shaped tip is no longer than 1 cm and comprises at least three sections including a first, a second and a third section. The second section is located distally from the first section and the third section is located distally from the second section. The second section may include a first material having a first durometer and a second material having a second durometer lower than the first durometer. The second material may include a polymer and tungsten. In some embodiments, first section includes the first material without the second material, and the third section includes the second material without the first material.

In some of the above embodiments, the first durometer is 35D and the second durometer is 25D. The forming and bonding step may include placing a first tube made of the first material partially over the distal end of the main body and heating the first tube such that it reflows onto the main body and bonds therewith. The forming and bonding step may further include placing a second tube made of the second material partially over a distal end of the first tube and heating the first tube and second tube such that they reflow and bond together. In some embodiments, the first tube and the second tube are each no longer than about 4 mm. In some embodiments, the first tube overlaps with the main body no more than about 2 mm and the second tube overlaps with the first tube no more than about 2 mm.

In some embodiments, the forming and bonding step further includes placing a tube made of heat shrink material over at least one of the first tube and the second tube, heating the heat shrink material until it shrinks and causes a diameter of at least one of the first tube and the second tube to shrink, and then removing the heat shrink material. The forming and bonding step may further include forming a taper on a distal end of the second tube by placing a tube made of heat shrink material over the distal end of the second tube, heating the heat shrink material until it shrinks and causes a diameter of distal end of the second tube to shrink more than a diameter of a proximal portion of the second tube, and then removing the heat shrink material.

The methods may further include a step of changing the shape of the first and second tubes after they have been reflowed together. This step may include using a mandrel or mold to hold the first and second tubes in a non-straight position while heating the first and second tubes to a temperature that is lower than a temperature that was used to reflow the first and second tubes together. This non-straight position may include a curve extending more than 90 degrees.

BRIEF DESCRIPTION OF THE DRAWINGS

The novel features of the disclosure are set forth with particularity in the claims that follow. A better understanding of the features and advantages of the present disclosure will be obtained by reference to the following detailed description that sets forth illustrative embodiments, in which the principles of the disclosure are utilized, and the accompanying drawings of which:

DETAILED DESCRIPTION

Described herein are catheter designs that allow a shaped tip to be more easily navigated through tortuous vasculature. Termination of the catheter at a flexible, soft tip is desirable to minimize vessel trauma. The added support of a rigid section in proximity to the distal tip further aides in catheter tracking as a flexible section (without support or reinforcement) would be prone to kink and excessive flexing.

Figure 1:
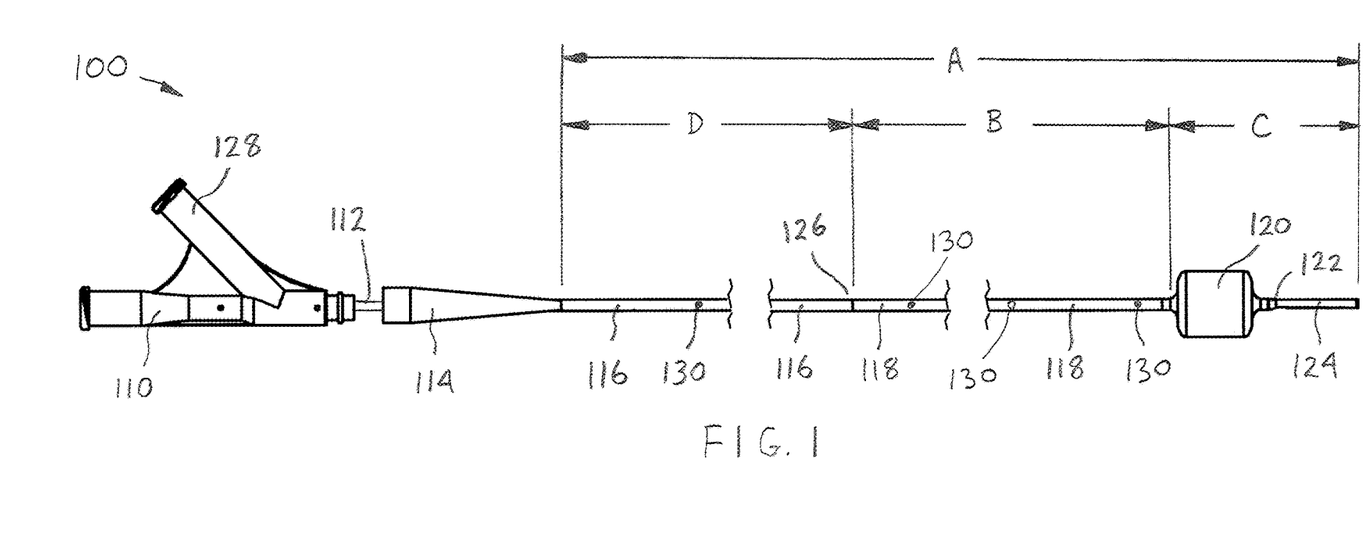
FIG. 1 is a fragmentary side view showing an exemplary vascular catheter system constructed according to aspects of the present disclosure.

As shown in FIG. 1, an exemplary vascular catheter system 100 constructed according to aspects of the present disclosure includes a Y-hub 110, an inner catheter 112, a strain relief 114, a proximal outer catheter section 116, a distal outer catheter section 118, an inflatable balloon 120, a marker band 122, and a distal tip segment 124. Y-hub 110 is shown separated from strain relief 114 for clarity in FIG. 1, but normally is connected thereto. Proximal outer catheter section 116 extends from inside Y-hub 110 to a junction point 126 with distal outer catheter section 118. Distal outer catheter section 118 extends from junction point 126 to the proximal end of balloon 120, and the proximal end of balloon 120 is fluidically sealed with the distal end of the distal outer catheter section 118. Proximal outer catheter section 116 may be joined to distal outer catheter section 118 with a butt joint weld at junction point 126 such that the outer catheter is fluid pressure tight. Inner catheter 112 extends from within Y-hub 110, through proximal outer catheter section 116, distal outer catheter section 118, balloon 120, marker band 122, and into the proximal end of distal tip segment 124. In this exemplary embodiment, the distal end of balloon 120 is fluidically sealed near the distal end of inner catheter 112. With this arrangement, a first generally annular volume (not shown) remains between an outer diameter of the inner catheter 112 and an inner diameter of the proximal outer catheter section 116. Similarly, a second generally annular volume (not shown) remains between the outer diameter of the inner catheter 112 and an inner diameter of the distal outer catheter section 118. These first and second generally annular volumes are in fluid communication with one another at junction point 126. In some embodiments, inner catheter 112 may be generally free to move laterally inside proximal outer catheter section 116 and distal outer catheter section 118. As such, inner catheter 112 may contact these outer catheter sections (as depicted in FIG. 4), and the generally annular volumes may become crescent shaped. What is meant by "generally annular volume" in the claims appended hereto is the space between inner catheter 112 and outer catheter sections 116 and 118, regardless of whether it always has an annular shape.

The first annular volume described above is in fluid communication inside Y-hub 110 with its lateral port 128. The second annular volume is in fluid communication with the interior of balloon 120. Accordingly, when a balloon inflation pressure is provided at lateral port 128, balloon 120 inflates as shown in FIG. 1. When the inflation pressure is removed from lateral port 128, balloon 120 deflates and returns to a retracted state (not shown) surrounding the distal region of inner catheter 112.

In some embodiments, catheter system 100 may have a working length A (i.e. outside of Y-hub 110 and strain relief 114) of about 50 cm to about 180 cm. In some embodiments, the length B of distal outer catheter section 118 is about 30 cm. In some embodiments, the diameter of balloon 120 is about 7 mm, its length is about 8 mm, and the length of distal tip segment 124 is about 8 mm. This results in a combined distance C of balloon and tip of about 1.5 cm, and a total distance B+C distal to junction point 126 of about 31.5 cm. For embodiments having a working length A of 150 cm, this leaves a length D of about 119.5 cm for the portion of proximal outer catheter section 116 that extends from Y-hub 110 and strain relief 114. In some implementations, catheter system 100 is introduced into the target vasculature through a diagnostic catheter (not shown.) In some of these implementations, it is desirable to have about 20 cm of flexible catheter section (e.g. B+C) extending from the diagnostic catheter in order to track through tortuous vasculature. Therefore, with the aforementioned dimensions, junction point 126 and the distal portion of proximal outer catheter section 116 remain inside the diagnostic catheter during a medical procedure.

Figure 2:
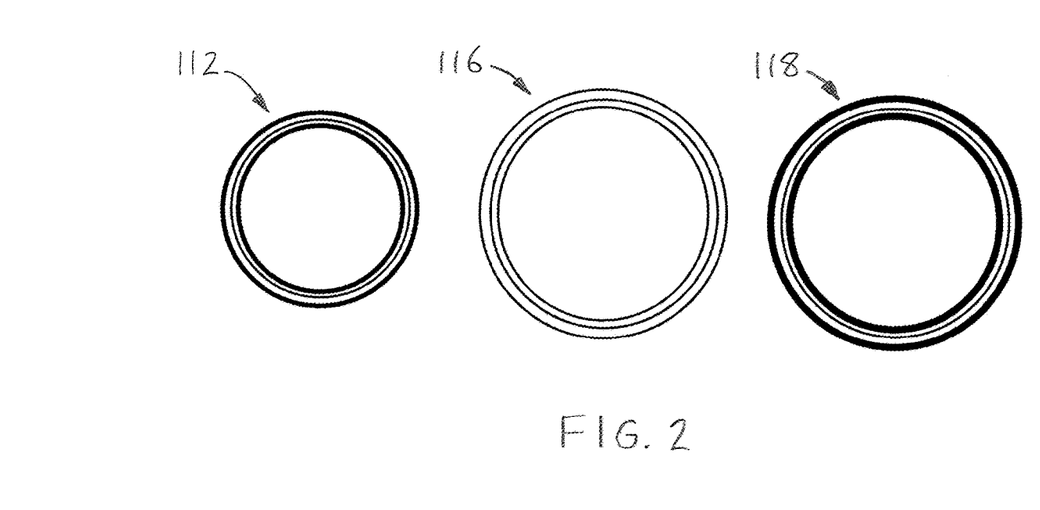
FIG. 2 is a cross-sectional view showing lateral cross-sections of an exemplary inner catheter, proximal outer catheter section, and distal outer catheter section.

Referring to FIG. 2, cross-sections of inner catheter 112, proximal outer catheter section 116, and distal outer catheter section 118 are shown. In this exemplary embodiment, each of these three components comprises an inner layer, a middle layer and an outer layer with the following characteristics:

|  | Inner catheter 112 | Proximal outer catheter section 116 | Distal outer catheter section 118 |
| --- | --- | --- | --- |
| Inside diameter (inches) | 0.020 | 0.032 | 0.032 |
| Outside diameter (inches) | 0.026 | 0.037 | 0.037 |
| Inner layer material | PTFE (Teflon) | Polyimide | Polyether block amide |
| Middle layer material | Stainless steel 304 braid; 0.0005" × 0.0025"; 16 wires; 100 PIC | Stainless steel 304 braid; 0.0005" × 0.0025"; 16 wires; 80 PIC | Stainless steel 304 braid; 0.0005" × 0.0025"; 16 wires; 75 PIC |
| Outer layer material | Polyether block amide 55 durometer | Polyimide & Nylon Skim coat | Polyether block amide |
| Other | 900 psi rating | 45 psi rating | 45 psi rating |

Figure 3A:
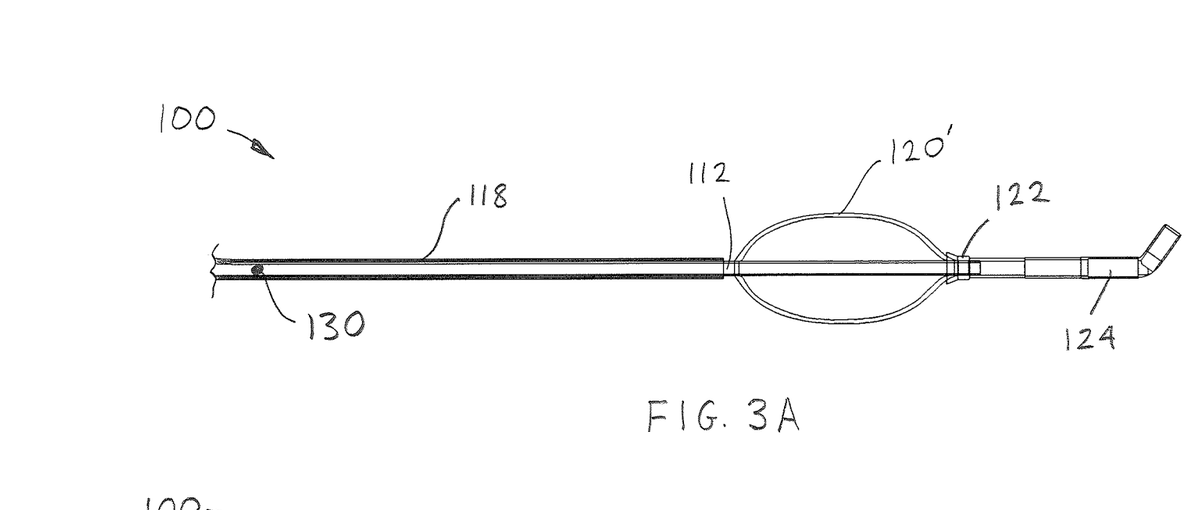
FIG. 3A is an enlarged side view showing the distal portion of a catheter system similar to the one shown in FIG. 1.
Figure 3B:
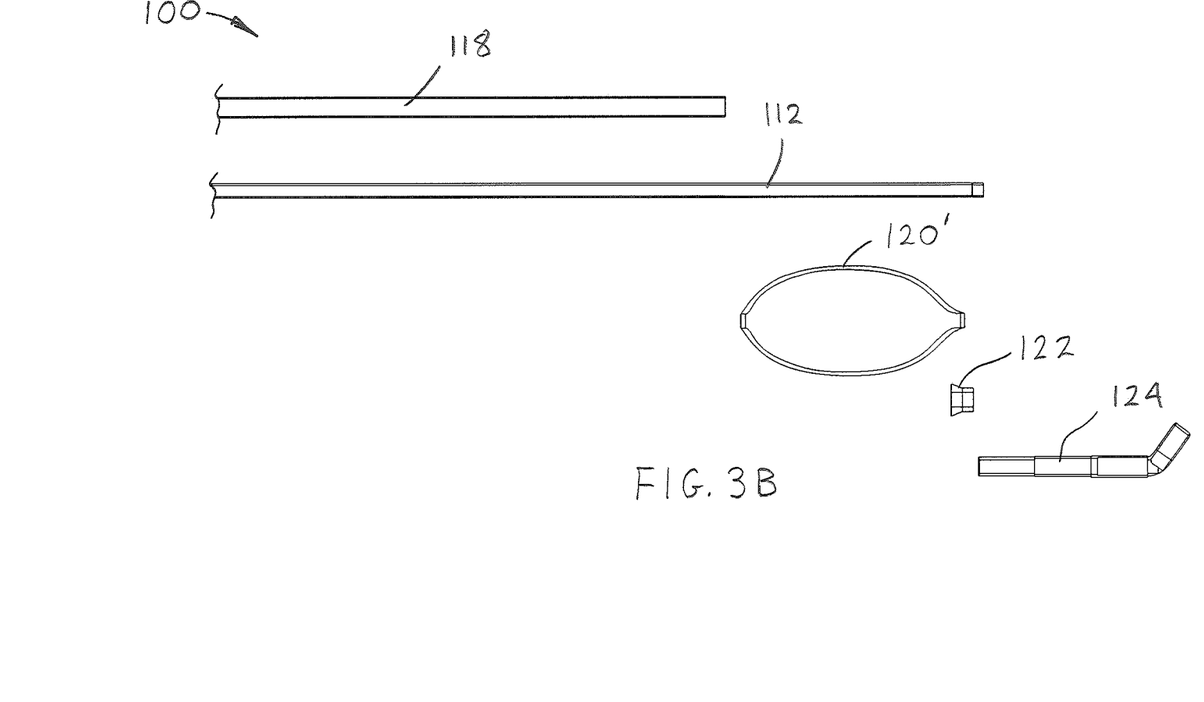
FIG. 3B is an exploded side view showing the distal portion of the catheter system of FIG. 3A.

Referring to FIGS. 3A and 3B, enlarged views showing the distal portion of catheter system 100 are provided. FIG. 3A shows an assembled view of the distal portion, and FIG. 3B shows an exploded view. Inflated balloon 120' shown in FIGS. 3A and 3B has a more rounded profile than that of balloon 120 shown in FIG. 1. As best seen in FIG. 3A, distal outer catheter section 118 stops just short of the proximal end of balloon 120'. To seal the proximal end of balloon 120' against the distal end of distal outer catheter section 118, a stepped inner sleeve and/or an outer sleeve (neither shown) may be utilized.

As shown in FIGS. 3A and 3B, distal tip segment 124 may be provided with a preset shape that extends a distal end thereof laterally outward. In this embodiment, the distal end extends outward at a 45 degree angle. In other embodiments, the distal end extends outward at an angle of about 60 to about 90 degrees (see for example FIG. 5). In still other embodiments, the tip angle can be between about 10 degrees and about 60 degrees, or between about 90 degrees and about 180 degrees (i.e. the tip can double back on itself.) In some later described embodiments, the tip can include two or more bends (see for example FIG. 6) rather than the single bend of the exemplary embodiment shown in FIGS. 3A-3B. This outward angle allows a medical practitioner to rotate the distal tip segment 124 towards a branch blood vessel (by rotating Y-hub 110 outside of the patient), extend a guidewire (not shown) distally from the distal tip segment 124 into the branch blood vessel, and then track the catheter system 100 over the guidewire into the branch blood vessel. This may be done repeatedly to track the catheter system 100 deep into tortuous vasculature toward target tissue.

As depicted in FIG. 3A, distal outer catheter section 118 may be connected to inner catheter 112 through at least one discrete connection point 130. In some embodiments, discrete connection point(s) 130 may be created by thermal or chemical bonding. For example, laser, radio frequency energy and/or a heated probe such as a soldering iron may be used to melt together the materials of distal outer catheter section 118 and inner catheter 112 to form a tack or spot weld. By way of another example, a hole may be formed in distal outer catheter section 118 and a small amount of glue, adhesive, epoxy or other fluid material may be injected into the hole to bond the two catheters 118 and 112 together. In the exemplary layout shown in FIG. 1, there may be one discrete connection point 130 formed between proximal outer catheter 116 and inner catheter 112, and three discrete connection points 130 formed between distal outer catheter section 118 and inner catheter 112. Further details of such discrete connection points 130 may be found in applicant's co-pending U.S. patent application Ser. No. 16/004,247 filed on Jun. 8, 2018 and entitled High Torque Catheter and Methods of Manufacture.

Referring to FIGS. 4A-4E, various exemplary shaped tips are schematically shown. In each of these examples, two or more layers of tubing are combined to create the tip construct. The left side of each figure represents the proximal end of the shaped tip, which is typically connected to the distal end of an inner catheter 112 as shown in FIGS. 3A-3B, and the right side of each figure represents the distal end of the shaped tip. Reference letters A-F and W denote discrete pieces of tubing which in some embodiments are each formed from different materials. The base material of tube A is formulated to bond to the main body of the catheter. W denotes a tube comprising tungsten, or in some embodiments another radio opaque material that serves as a location marker under fluoroscopy or other imaging during a surgical procedure. In other embodiments, W may simply denote another material similar to the materials of A-F (i.e. not having any special radio opaque properties.) The shaped tips disclosed herein may be used at the distal end of catheters with or without balloons.

Figure 4A:
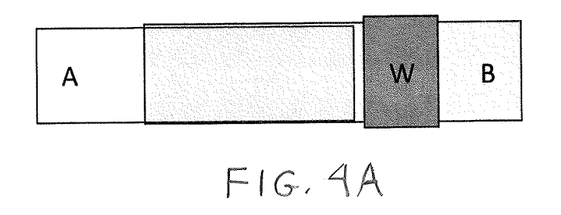
FIGS. 4A, 4B, 4C, 4D and 4E are a series of side views schematically showing various exemplary shaped tips.

In the construct depicted in FIG. 4A, a tube A comprising a first polymeric material (such as a polyether block amide, or PEBA) is placed within a tube B comprising a second polymeric material (which may also be a PEBA.) In this embodiment, the material of tube B is softer, more flexible and has a lower durometer than the material of tube A. Tube W, comprising tungsten, is placed over the distal end of tube B and located just distal to the middle region where tubes A and B are overlapping.

Tube A may be oversized so that its proximal end slides over the distal end of inner catheter 112. Heating tube A (before or after tubes B and W are added) allows tube A to shrink to fit over inner catheter 112. The three tubes A, B and W may then be heated to melt and bond together and to inner catheter 112 using a material reflow process. The multiple layers may be processed in parallel or in series. In the middle section of FIG. 4A where tubes A and B overlap, the materials of tubes A and B may blend together in the reflow process such that the middle section no longer has discrete layers but rather comprises a blend of materials. Temperature profiles, time and other parameters of the shrink to fit and/or reflow process may vary based on material selection, diameter and thickness. In some embodiments, materials A, B and W each have a different color which may blend together during the reflow process or may remain distinct. With this disclosed fabrication method, material selection and layering can create different bend profiles of the shaped tip, offering transition from rigid to flexible in a gradient rather than abrupt transition(s), which can reduce kinking of the catheter tip. The construct depicted in FIG. 4A includes the characteristics of having a strong hold to its shape, relatively thick walls, and a radio opaque marker near its distal tip, but can be difficult to manufacture.

Figure 4B:
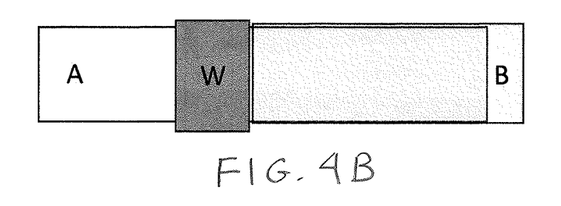

Referring to FIG. 4B, a shaped tip similar to the construct shown in FIG. 4A is provided. In this example, the region of overlap between tubes A and B is longer, the length which tube B extends distally from the overlap region is shorter, and tube W is located proximal to the overlap region rather than distal to it as in the example shown in FIG. 4A. The construct depicted in FIG. 4B includes the characteristics of having a good hold to its shape, relatively thick walls, a radio opaque marker away from its distal tip, and is less difficult to manufacture than the tip shown in FIG. 4A.

Figure 4C:
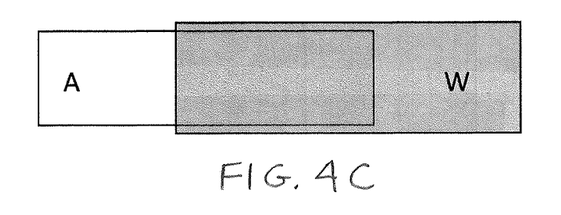

Referring to FIG. 4C, a shaped tip similar to the construct shown in FIG. 4A is provided. In this example, there are only two tubes used: A and W. Instead of having only a narrow marker band W as shown in FIG. 4A, the entire distal tube W may comprise a radio opaque material such as tungsten, as shown in FIG. 4C. In this exemplary embodiment, the material of tube W is softer, more flexible and has a lower durometer than the material of tube A. The construct depicted in FIG. 4C includes the characteristics of having a good hold to its shape, a radio opaque marker that extends to its distal tip, has less of a flexibility/rigidity gradient, and is fairly easy to manufacture compared with the previously described tips.

Figure 4D:
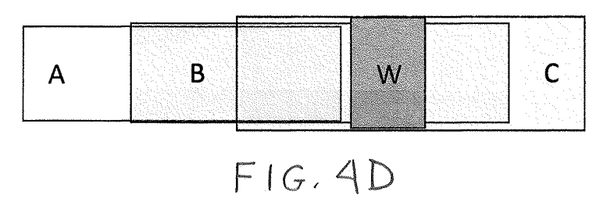

Referring to FIG. 4D, a shaped tip similar to the construct shown in FIG. 4A is provided. In this example, a forth material C is used. Each of the materials A, B and C gets progressively softer, more flexible and has a lower durometer moving distally. As depicted in FIG. 4D, there are six regions of the shaped tip of this embodiment (proximal to distal): A, A+B, A+B+C, B+C+W, B+C and C.

Figure 4E:
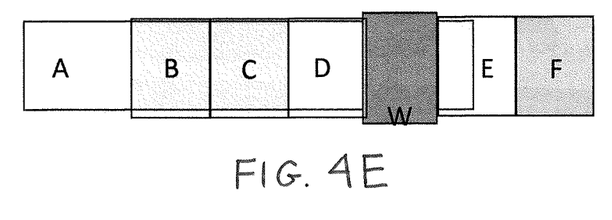

Referring to FIG. 4E, a shaped tip similar to the construct shown in FIG. 4C is provided. In this example, seven materials are used. Each of the materials A, B, C, D, E, and F gets progressively softer, more flexible and has a lower durometer moving distally. As depicted in FIG. 4E, there are eight regions of the shaped tip of this embodiment (proximal to distal): A, A+B, A+C, A+D, A+W, A+E, E and F. Tubes B, C and D abut rather than overlap with one another, as do tubes E and F. Since tube A extends only partway through tube E in this embodiment, tubes E and F may be temporarily mounted over a mandrel when fusing them together to ensure proper alignment. The constructs of FIGS. 4D and 4E have more of a flexibility/rigidity gradient than the previously described embodiments. Material wall thicknesses may also be varied to further tune performance and behavior of the tip.

In the exemplary embodiments depicted in FIGS. 4A-4E, when there is an overlapping joint rather than a butt joint between two tubes, the more distal of the two tubes slides over the more proximal tube. This is done so that if an edge of the outer (distal) tube remains after the manufacture of the shaped tip is complete, it will not impede the insertion of the tip into a patient's vasculature. If such an outer edge does remain after manufacture, it may increase friction and/or catch on features of tortuous vasculature when the shaped tip is being withdrawn with the catheter from the patient. However, this is less of an issue during removal of the catheter because the catheter is in tension during removal, as opposed to being in compression during insertion when the catheter may tend to buckle rather than advance through the vasculature. In alterative embodiments (not shown), the more proximal of the two tubes may be slid over the more distal tube during manufacture.

Figure 5:
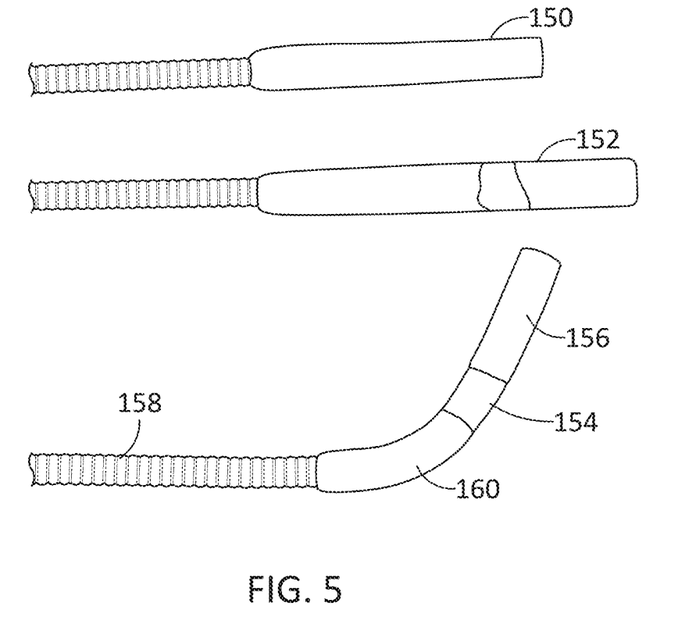
FIG. 5 is a plan view showing three catheter tips in various stages of manufacture.

Referring to FIG. 5, three catheter tips are shown in various stages of manufacture. All three tips are formed using a layering process similar to that shown in FIG. 4A as previously described. Catheter tip 150 uses materials that are generally the same color so that the various layers are not readily apparent after they have been reflowed together. Tip 152 uses materials A, W and B that each have a different color. In some embodiments such as this, the material colors remain distinct after the reflow process. In other embodiments (not shown), colors of the various overlapping materials blend together such that the distinct tube materials are no longer readily discernable.

After a straight catheter tip is formed, such as previously described, it may be shaped into a non-straight configuration. For example, tip 150 shown in FIG. 5 may be used in its straight configuration while tip 152 may be formed into a curved tip 154 as shown. A low temperature may be used to set the material to a desired shape after the reflow process described above. Holding the material in the desired shape while at a temperature that is below the reflow temperature, such as 225 degrees F. for approximately 120-180 seconds for a layered construct of PEBA tubes, can change the overall shape of the tip without altering its dimensional aspects. These temperature and time parameters work for a convection based technique after a shaping mandrel having the desired shape is inserted through the distal end of the central lumen of the tip. An outer mold or tool with the desired shape may be used instead of or in conjunction with the mandrel. If the tip is in contact with media other than air, the temperature may need to be adjusted to ensure no dimensional changes occur during the shape changing process. For example, if the tip is held in a glass or aluminum fixture, etc., a temperature of 110-150 F may be needed, and it may be held at this temperature for less time. As shown in FIG. 5, the shaped tip 154 of this exemplary embodiment has a straight distal portion 156 configured to deviate from the longitudinal axis of the main body 158 of the catheter when tip 154 is in its relaxed state. The straight distal portion 156 extends through an angle of about 70 degrees from the longitudinal axis. A curved portion 160 may be provided between straight distal portion 156 and main body 158 as shown. In this exemplary embodiment, curved portion 160 has an inside bend radius of about 0.10 inches, or about 3 times the outside diameter of the tubing forming the tip 154. This tight bend radius allows the catheter tip to be maneuvered through tighter turns in the vasculature. In other embodiments, the bend radius may be smaller or larger. In some embodiments, the bend radius is no smaller than about 0.015 inches, as a bend radius smaller than this in a tube of the same diameter is difficult to traverse with a guidewire.

Figure 6:
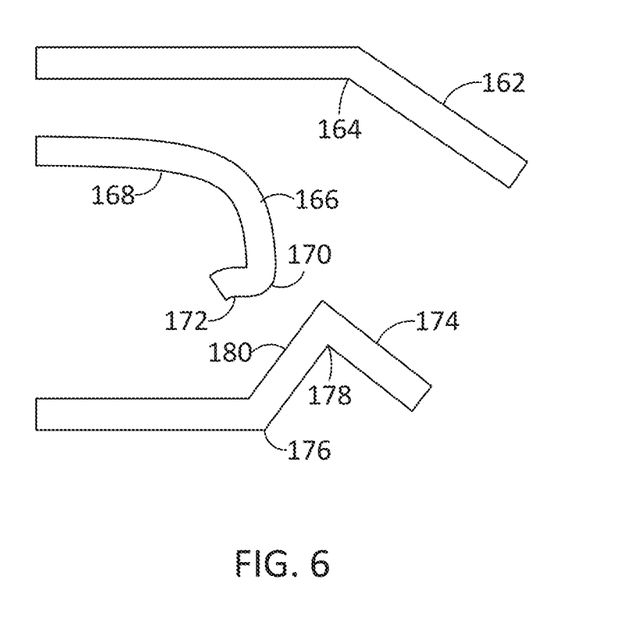
FIG. 6 is a plan view schematically showing three more examples of shaped catheter tips.

Referring to FIG. 6, three more examples of shaped catheter tips are schematically shown. Tip 162 is similar to tip 154 in FIG. 5, but has a sharper bend 164. Tip 166 includes three bends 168, 170 and 172. First bend 168 has a bend radius that becomes increasingly smaller towards the distal tip. Second bend 170 has a tighter bend radius in the same direction as first bend 168. Together, bends 168 and 170 turn tip 166 about 180 degrees, forming a hook shape. Third bend 172 has a bend radius that is larger than those of bends 168 and 170, and bends in the opposite direction. Tip 174 includes two sharp bends 176 and 178, each bending in opposite directions and separated by a straight section 180. Various other combinations of single or multiple bend shaped tips are possible using the manufacturing techniques disclosed herein. For example, a J-shaped tip similar to tip 166 may have a single, continuous bend of constant radius and may extend 180 degrees, between 120 and 160 degrees, or other angle.

Figure 7A:
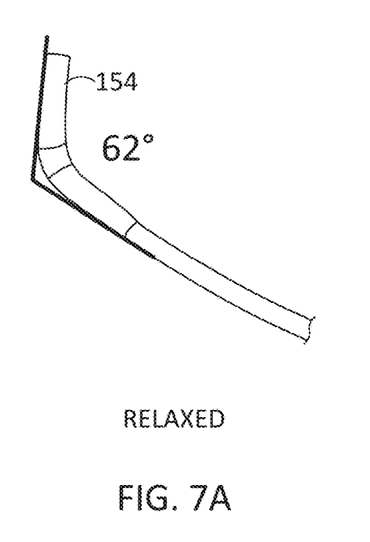
FIGS. 7A, 7B, 7C and 7D, are a series of plan views showing a shaped tip being progressively straightened by advancing a guidewire through it.
Figure 7B:
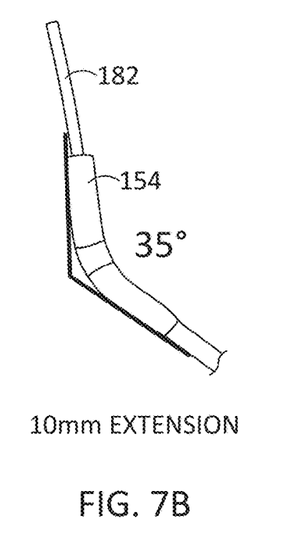
Figure 7C:
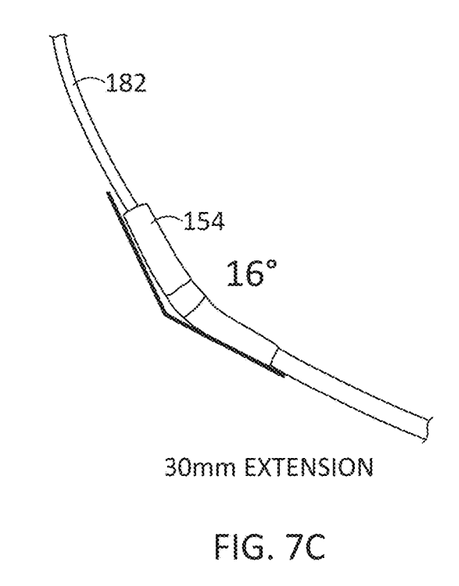
Figure 7D:
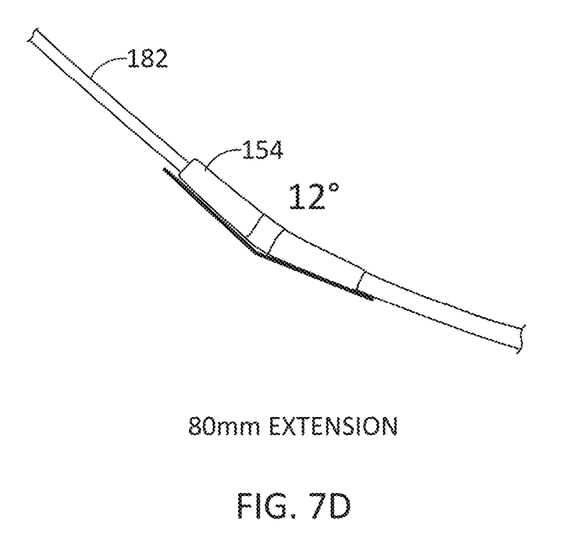

Referring to FIGS. 7A-7D, a series of images are provided showing shaped tip 154 progressively straightened by advancing a guidewire through it. As previously described, the catheter and shaped tip 154 are provided with a central lumen configured to receive a flexible guidewire 182. FIG. 7A shows shaped tip 154 in a relaxed state and having a deflection angle of 62 degrees. When the distal tip of guidewire 182 is passed through shaped tip 154 as shown in FIG. 7B, the stiffness of guidewire 154 causes tip 154 to move towards a straighter configuration (i.e. to have an angle of deviation of less than 62 degrees from the longitudinal axis of the main body 158), such as 35 degrees in this case. A guidewire may be used that increases in stiffness moving from its distal end towards its proximal end. When such a guidewire 182 is advanced further through tip 154, it causes tip 154 to further straighten towards the longitudinal axis of the catheter. In this exemplary embodiment, a 10 mm extension of guidewire 182 through tip 154 causes it to straighten to 35 degrees as shown in FIG. 7B, an extension of 30 mm causes an angle of 16 degrees as shown in FIG. 7C, and an extension of 80 mm causes an angle of 12 degrees as shown in FIG. 7D. A surgeon can thus steer tip 154 through turns in a patient's vasculature by adjusting the angle of the tip with the depth of guidewire 182.

Prior art shaped tips are typically made of a single material and often have lengths between about 1.5 and 3.0 cm in length. Using the fabrication techniques disclosed herein, similar bend profiles can be achieved in a shorter distance. In some embodiments, the lengths of the inventive tips extending beyond the base catheter are between 0.3 and 1.0 cm. These shorter lengths allow for the catheter to be maneuvered through tighter turns in the vasculature while minimizing the distance from the distal tip of the catheter to an operational interface such as a balloon. This allows accurate positioning of the operational interface and distal tip for the desired application, such as therapeutic delivery.

In one particular exemplary embodiment, a shaped tip is formed from two Pebax® tubes in a starting configuration similar to that shown in FIG. 4C. Tube A is made of a 35 durometer Pebax® infused with 40% barium sulfate to increase lubricity. A stabilizer may also be added so the material can withstand higher temperatures for longer periods of time, and longer exposure to ultraviolet/fluorescent light. In this embodiment, the inside diameter of tube A is 0.031"±0.0005", the wall thickness is 0.004"±0.0005", the concentricity is >85% and the length is 4.0 mm. Tube W is made of 25 durometer Pebax® infused with 70% tungsten by weight. A stabilizer may also be added to tube W. The inside diameter, wall thickness, tolerances and length for tube W are the same as for tube A.

In this exemplary embodiment, the following steps may be performed to form and bond the distal tip on the end of an inner catheter:

1. Set a heat box to 325° F.±5° F. & 25 SCFH.
2. Trim the distal end of the inner catheter to 3±0.5 mm from the distal edge of outer catheter.
3. Insert a 0.020" diameter mandrel into distal end of the inner catheter (≥2 cm.) Utilization of the mandrel controls the inside diameter and concentricity of all the tubing involved during the reflow process.
4. Place a heat shield over the inner catheter adjacent to the marker band (which is located proximal to the distal end of the inner catheter.)
5. Slide tube A onto the distal end of the inner catheter with a 2 mm overlap.
6. Place a RNF heat shrink tube over tube A and heat in heat box for 35-40 sec.
7. Skive the RNF tube with a razor blade, being careful not to cut through the RNF layer, and peel away the RNF layer.

8. Slide tube W onto tube A with a 1.75 to 2.00 mm overlap with tube A, making sure to leave a small gap (0.25 mm) between the proximal end of tube W and the distal end of the inner catheter. NOTE: This gap should close during the reflow process.
9. Place a RNF heat shrink tube over both tube A and Tube W (all layers) and heat for 35-40 sec.
10. Skive the RNF tube with a razor blade, being careful not to cut through the RNF layer, and peel away the RNF layer.
11. Trim distal tip to 7±1 mm from the distal edge of the inner catheter.

After the above reflow process, the following steps may be performed to create a taper on the distal tip:
1. Set the heat box to 325° F.±5° F. & 25 SCFH.
2. Insert a 0.020" diameter mandrel into distal end of catheter (≥2 cm).
3. Place a RNF heat shrink tube over the distal tip assembly.
4. Starting at distal end of the RNF tube, heat≤0.5 mm on to tube W for 2-5 sec.
5. Visually inspect under microscope to confirm taper on distal edge.

After the above taper process, the following steps may be performed to shape the distal tip:
1. Set the heat box to 230° F.±10° F.
2. Set air flow to 40±5 SCFH.
3. Slide the straight tip onto a shaping mandrel. Note that to create a 90 degree bend in the tip, a mandrel having a 105 degree bend is used since the tip material will relax back to about 90 degrees after the shaping process in complete.
4. Slide the tip up to a mandrel stop around the bend to 12 mm±0.5 mm from the end of the mandrel.
5. Place the tip and mandrel into the heat box for 3 mins±10 s. Start heating at tube A and slowly move toward the distal end of tube W.
6. Keep the mandrel in the tip until it cools.

In another embodiment similar to the construct shown in FIG. 4A, a 55 durometer Pebax® tube with BaSO4 additive is used as tube A, a 35 durometer Pebax® tube is used as tube B, and a 25 durometer Pebax® tube with Tungsten is used as tube W. A temperature approximately 25° F. higher may be needed to process tube A due to its higher durometer.

The shaped catheter tips disclosed herein created by layering or abutting different materials can offer improved bend profiles, transition from rigid to flexible in a gradient rather than abrupt changes which in turn can reduce kinking of the catheter tip, and can provide sharper bends in a shorter length of catheter tip in order to more easily navigate through tight bends in the vasculature.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the disclosure. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the FIGS. is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present disclosure.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

In general, any of the apparatuses and methods described herein should be understood to be inclusive, but all or a sub-set of the components and/or steps may alternatively be exclusive, and may be expressed as "consisting of" or alternatively "consisting essentially of" the various components, steps, sub-components or sub-steps.

As used herein in the specification and claims, including as used in the examples and unless otherwise expressly specified, all numbers may be read as if prefaced by the word "about" or "approximately," even if the term does not expressly appear. The phrase "about" or "approximately"

may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the disclosure as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the disclosure as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" or "disclosure" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A vascular catheter system comprising:
a flexible main body which extends along a generally straight longitudinal axis when in a relaxed state, the main body having a proximal end and a distal end, the main body having a lumen therethrough configured to slidably receive a guidewire; and
a flexible shaped tip coupled to the distal end of the main body such that a radially outermost surface of a proximal end of the shaped tip is disposed radially about a distal region of the main body, the shaped tip having a lumen therethrough in communication with the lumen of the main body and configured to slidably receive the guidewire, the shaped tip having at least a portion configured to deviate from the longitudinal axis when in a relaxed state and configured to move towards alignment with the longitudinal axis when the guidewire is extended through the lumen of the shaped tip,
wherein the shaped tip is no longer than 1 cm and comprises at least three sections including a first, a second and a third section, the second section being located distally from the first section and the third section being located distally from the second section,
the second section comprising a first material having a first durometer and a second material having a second durometer lower than the first durometer, the second material comprising a polymer and tungsten, the first section comprising the first material without the second material with the first material extending from a proximal end of the first section to a distal end of the first section and the first material forming the radially outermost surface of the proximal end of the shaped tip, and the third section comprising the second material without the first material, the second and third sections being radiopaque, wherein the first and second materials each extend completely around the second section from a proximal end of the second section to a distal end of the second section.

2. The catheter system of claim 1, wherein the at least one portion of the shaped tip configured to deviate from the longitudinal axis extends through an angle of at least 30 degrees.

3. The catheter system of claim 1, wherein the at least one portion of the shaped tip configured to deviate from the longitudinal axis extends through an angle of between about 60 degrees and about 90 degrees.

4. The catheter system of claim 1, wherein the at least one portion of the shaped tip configured to deviate from the longitudinal axis extends through an angle of between about 120 degrees and about 160 degrees.

5. The catheter system of claim 1, further comprising the guidewire configured to be received through the main body and the shaped tip to guide a distal end of the shaped tip through torturous vasculature.

6. The catheter system of claim 5, wherein a distal region of the guidewire increases in stiffness when moving from its distal end towards its proximal end.

7. The catheter system of claim 1, further comprising an inflatable balloon located near the distal end of the main body.

8. The catheter system of claim 1, wherein the shaped tip comprises a single bend.

9. The catheter system of claim 1, wherein the shaped tip comprises at least two bends.

10. The catheter system of claim 1, wherein the shaped tip comprises a curved portion having an inner bend radius no greater than about 0.10 inches.

11. The catheter system of claim 1, wherein the shaped tip comprises a curved portion having an inner bend radius no greater than about three times an outside diameter of the shaped tip.

12. The catheter system of claim 1, wherein the main body comprises an inner shaft within and radially spaced from an outer shaft of the main body, the radial spacing between the inner and outer shafts defining an inflation lumen, and the inner shaft extending distally beyond a distal end of the outer shaft.

13. The catheter system of claim 12, wherein the inner shaft has a length from a proximal end of the inner shaft to a distal end of the inner shaft, wherein the shaped tip is coupled to the distal end of the inner shaft such that the radially outermost surface of the proximal end of the shaped tip is disposed radially about a radially outermost surface of the inner shaft, the radially outermost surface of the inner shaft being the radially outermost surface of the inner shaft along the length of the inner shaft.

* * * * *